United States Patent
Hiramura et al.

(10) Patent No.: US 10,292,934 B2
(45) Date of Patent: *May 21, 2019

(54) DISINTEGRATING PARTICLE COMPOSITION CONTAINING ACID-TYPE CARBOXYMETHYLCELLULOSE AND CRYSTALLINE CELLULOSE, AND ORALLY DISINTEGRATING TABLET CONTAINING SAID COMPOSITION

(71) Applicants: DAICEL CORPORATION, Osaka (JP); NICHIRIN CHEMICAL INDUSTRIES, LTD., Hyogo (JP)

(72) Inventors: Takahiro Hiramura, Tokyo (JP); Kiyoshi Ikura, Hyogo (JP); Sae Ishikawa, Hyogo (JP); Tomohito Okabayashi, Hyogo (JP); Naohiro Hashikawa, Hyogo (JP); Tetsuro Morita, Hyogo (JP); Kimiko Ikeda, Hyogo (JP)

(73) Assignees: DAICEL CORPORATION, Osaka (JP); NICHIRIN CHEMICAL INDUSTRIES, LTD., Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/426,669

(22) PCT Filed: Sep. 13, 2013

(86) PCT No.: PCT/JP2013/074823
§ 371 (c)(1),
(2) Date: Mar. 6, 2015

(87) PCT Pub. No.: WO2014/046035
PCT Pub. Date: Mar. 27, 2014

(65) Prior Publication Data
US 2015/0238424 A1    Aug. 27, 2015

(30) Foreign Application Priority Data
Sep. 20, 2012 (JP) ................. 2012-206897

(51) Int. Cl.
*A61K 9/20* (2006.01)
*A61K 9/00* (2006.01)

(52) U.S. Cl.
CPC .......... *A61K 9/2059* (2013.01); *A61K 9/0056* (2013.01); *A61K 9/2018* (2013.01); *A61K 9/2027* (2013.01); *A61K 9/2054* (2013.01)

(58) Field of Classification Search
None
See application file for complete search history.

(56) References Cited

U.S. PATENT DOCUMENTS

| 2,851,453 A | 9/1958 | Kennon et al. |
| 2011/0053942 A1* | 3/2011 | Fujiwara ............... A61K 9/0056 |
|  |  | 514/239.5 |

FOREIGN PATENT DOCUMENTS

| EP | 1 980 272 A2 | 10/2008 |
| EP | 2 251 005 A1 | 2/2009 |
| JP | 10-182436 A | 7/1998 |
| JP | 2000-273039 | 10/2000 |
| JP | 2002-179558 | 6/2002 |
| JP | 2007-153887 A | 6/2007 |
| JP | 2008-285434 | 11/2008 |
| JP | 4551627 | 9/2009 |
| JP | 2010-529074 A | 8/2010 |
| JP | 2012-31138 | 2/2012 |
| JP | 2013-147470 | 8/2013 |
| TW | 1 376 243 | 11/2012 |
| WO | 2009/102038 | 8/2009 |
| WO | 2011/019043 A1 | 2/2011 |
| WO | 2011/019045 | 2/2011 |
| WO | 2012/087377 A1 | 6/2012 |
| WO | 2013/146917 A1 | 10/2013 |

OTHER PUBLICATIONS

Extended European Search Report issued in European Patent Application No. 13 84 0080, dated Feb. 11, 2016.
International Search Report, issued in International Patent Application No. PCT/JP2014/075241, dated Dec. 22, 2014.
International Search Report in International Patent Application No. PCT/JP2013/059083 dated Jun. 25, 2013.
International Search Report in International Patent Application No. PCT/JP2013/074823 dated Oct. 15, 2013.

* cited by examiner

*Primary Examiner* — David J Blanchard
*Assistant Examiner* — Daniel F. Coughlin
(74) *Attorney, Agent, or Firm* — Ping Wang; Morris, Manning & Martin, LLP

(57) ABSTRACT

An object of the present application is to provide an orally-disintegrating tablet having excellent tablet hardness and disintegrability, and including a disintegrative particulate composition. This invention relates to a disintegrative particulate composition comprising the four components consisting of a first disintegrator component of an acid-type carboxymethylcellulose, a second disintegrator component other than the acid-type carboxymethylcellulose, an excipient of a sugar or sugar alcohol, and crystalline cellulose; and to an orally-disintegrating tablet, including the disintegrative particulate composition and a medicinal ingredient.

3 Claims, No Drawings

DISINTEGRATING PARTICLE COMPOSITION CONTAINING ACID-TYPE CARBOXYMETHYLCELLULOSE AND CRYSTALLINE CELLULOSE, AND ORALLY DISINTEGRATING TABLET CONTAINING SAID COMPOSITION

TECHNICAL FIELD

The present invention relates to a disintegrative particulate composition which comprises an acid-type carboxymethylcellulose and a crystalline cellulose, and an orally-disintegrating tablet including the composition.

BACKGROUND ART

In the past, orally-disintegrating tablets have been developed as highly convenient forms which can safely be taken by patients who have difficulty in swallowing drugs, elderly people, children, etc. and which can easily be taken without water. It is important that orally-disintegrating tablets have sufficient breaking strength (tablet hardness) such that any cracks, powdering, etc. are not caused in the tablets during production or transportation of the tablets or during breaking the seals in the same manner as general tablets, and also, it is important that orally-disintegrating tablets have excellent disintegrability (disintegration time) such that the tablets immediately disintegrate in the oral cavity.

The tablet hardness and disintegrability are mutually opposing properties. In general, when a molding pressure is increased to increase the hardness, the disintegration time tends to be prolonged, and, when the molding pressure is reduced to shorten the disintegration time, the hardness tends to be smaller. Therefore, various technologies have been developed in order to cope with both the two properties or to achieve an optimal balance between the two properties.

Furthermore, components of the particles, granulation methods, etc. have been studied in order to impart superior moldability to particles or particulate compositions constituting tablets.

Additionally, an acid-type carboxymethylcellulose is a cellulose derivative otherwise called "carmellose", and this substance has properties that, when water is added to the substance, the substance swells but converts into a suspension having almost no viscosity. Therefore, an acid-type carboxymethylcellulose has been used as an ingredient for orally-disintegrating tablets, namely as a base, binder, excipient or disintegrator therefor.

Also, a crystalline cellulose is a white water-insoluble powdery substance obtained by partially depolymerizing α-cellulose, which is obtained from fibrous plants, with acids, followed by purification. A crystalline cellulose has no taste, and, since the substance is chemically inactive, it does not change even when being mixed with medicaments. Therefore, a crystalline cellulose has been used for purposes of a pharmaceutical additive, in particular, an excipient, binder, disintegrator or the like for preparing tablets. In addition, a crystalline cellulose has been used as an emulsification stabilizer or the like for cosmetics, dairy products, etc. besides an additive for pharmaceuticals.

For example, PTL 1 describes a disintegrative particulate composition which is produced through homogeneous dispersion of mannitol, xylitol, an inorganic excipient, a disintegrator and carmellose in the presence of water, followed by drying the dispersion. The composition is characterized in that composite particles including xylitol dispersed in mannitol particles in the solid state are formed, and that the inorganic excipient, the disintegrator and carmellose are dispersed in the composite particles. The disintegrative particulate composition is produced through spray granulation of a dispersion obtained by dispersing these components in an aqueous medium, or is produced by spraying the dispersion to carriers such as of mannitol.

Although crospovidone and crystalline cellulose and the like are described as the disintegrator in PTL 1, there is no specific example of a disintegrative particulate composition that simultaneously comprises both crospovidone and crystalline cellulose. PTL 1 also discloses that the inorganic excipient has a function of controlling water-concentration in the tablet to reduce the water content so that it will promote the reduction of a binding force at joining points between the disintegrative particle compositions. Thus, the inorganic excipient is an essential component for obtaining an excellent disintegrability in the invention disclosed in PTL 1.

Furthermore, it is also an essential requirement that mannitol and xylitol comprised in the integrative particulate composition have to form the "composite particles" having the above-mentioned particular structure.

Also, PTL 2 describes an orally-disintegrating tablet which contains an active ingredient and 10% (w/w) or more of carboxymethylcellulose relative to the total amount. The components are mixed, and then, the orally-disintegrating tablet is prepared with a tablet machine.

Moreover, PTL 3 describes a method of producing an orally-disintegrating tablet which contains loratadine as a medicinal ingredient. This production method is characterized in that two-stage granulation steps are carried out therein, i.e. loratadine and at least one type of an additive such as a binder, excipient, or disintegrator are granulated in the first granulation step, and, in the second granulation step, granules obtained in the first granulation step are further granulated together with at least one type of the same additive such as a binder, excipient, or disintegrator as that used in the first granulation step. As one example of the disintegrator, carmellose is mentioned therein.

Furthermore, PTL 4 describes a method of producing an orally-disintegrating tablet. The production method includes a step of spraying a water suspension of a water-soluble but hydrophilic disintegrating component onto a mixture of an excipient and a medicament to obtain granules A including the medicament; a step of spraying the same water suspension of the disintegrating component onto the excipient to obtain granules B not including the medicament; and a step of subjecting the resulting granules A and B to compression molding.

RELATED ARTS

Patent Literature

PTL 1: International Publication Pamphlet No. WO 2011/019045
PTL 2: JP-A-2008-285434
PTL 3: JP-A-2012-31138
PTL 4: Specification of Japanese Patent No. 4551627

SUMMARY OF INVENTION

Problems to be Solved by the Invention

A problem was observed in conventional technologies, in which, when producing a disintegrative particulate composition and an orally-disintegrating tablet including the composition, addition of a crystalline cellulose as an excipient increased the tablet hardness but reduced the disintegrability (prolonged the disintegration time).

Accordingly, an object of the present invention is to solve such a problem, and thus, is to provide a disintegrative particulate composition that has on one hand tablet hardness comparable to that of the conventional disintegrative particle composition comprising the crystalline cellulose, and on the other hand that can show more excellent disintegrability (shorter disintegration time), and to provide an orally-disintegrating tablet including said composition.

Means to Solve the Problem

The present inventors carried out intensive studies in order to solve the above-described problems. Consequently, the present inventors found that more excellent disintegrability (shorter disintegration time) than and comparable tablet hardness to those of the conventional disintegrative particle composition can be obtained, by making the following four components to coexist: a first disintegrator component of an acid-type carboxymethylcellulose; a second disintegrator component other than the acid-type carboxymethylcellulose; an excipient of a sugar or sugar alcohol, and crystalline cellulose, leading to completion of this invention. More specifically, the present invention is to provide the following aspects.

[Aspect 1]

A disintegrative particulate composition comprising the four components consisting of a first disintegrator component of an acid-type carboxymethylcellulose, a second disintegrator component other than the acid-type carboxymethylcellulose, an excipient of a sugar or sugar alcohol, and crystalline cellulose.

The disintegrative particulate composition according to Aspect 1, wherein the second disintegrator component is one or more components selected from crospovidone, sodium croscarmellose, sodium carboxymethyl starch, low substituted hydroxypropylcellulose, calcium carboxymethylcellulose, hydroxypropyl starch, and starch.

[Aspect 3]

An orally-disintegrating tablet, including the disintegrative particulate composition according to Aspect 1 or 2 and a medicinal ingredient.

[Aspect 4]

The orally-disintegrating tablet according to Aspect 3, having a hardness of 50 to 150 N and a disintegration time in water of 10 to 30 seconds.

Advantageous Effects of Invention

By making the following four components consisting of the first disintegrator component of an acid-type carboxymethylcellulose, the second disintegrator component other than the acid-type carboxymethylcellulose, the excipient of a sugar or sugar alcohol, and crystalline cellulose, excellent tablet hardness and disintegrability desired for an orally-disintegrating tablet can be imparted to it, and excellent moldability can be provided in production of said tablet as well.

For the purpose of obtaining said advantages of the present invention, it is not necessary for the inorganic excipient to be comprised in the orally-disintegrating tablet, or for mannitol and xylitol comprised in the disintegrative particulate composition to form the "composite particles" having the above-mentioned particular structure, as are, however, required in the invention disclosed in PTL 1.

DETAILED DESCRIPTION

The present invention relates to the disintegrative particulate composition comprising the four components consisting of the first disintegrator component of an acid-type carboxymethylcellulose, the second disintegrator component other than the acid-type carboxymethylcellulose, the excipient of a sugar or sugar alcohol, and crystalline cellulose. Said composition does not comprise the inorganic excipient.

Four mechanisms of "wicking", "swelling", "deformation" and "repulsion" have been proposed as mechanisms of disintegration of tablets or the like. Among them, "wicking" is a disintegration mechanism which proceeds upon weakened binding force between particles included in the tablet as a result of water permeation through components such as disintegrators included in the tablet. As a typical example of a disintegrator having a higher effect to promote such "wicking", an acid-type carboxymethylcellulose has been known. Also, "swelling" is a disintegration mechanism which proceeds upon swelling of disintegrators themselves as a result of water permeation through the disintegrators.

The acid-type carboxymethylcellulose, which is the first disintegrator component included in the disintegrative particulate composition of the present invention, is a substance called carmellose, and has been used as a pharmaceutical additive. In the same manner as the acid-type carboxymethylcellulose, for example, both a calcium salt of carboxymethylcellulose and a cross-linked product of carboxymethylcellulose sodium are water-insoluble, and have been used as disintegrator for tablets, etc. On the other hand, a sodium salt of carboxymethylcellulose is water-soluble, and has been used for purposes of a binder, etc. In addition, in some cases, a salt of carboxymethylcellulose may be referred to as carmellose.

For the second disintegrator component of the disintegrative particulate composition of the present invention, any disintegrators other than the acid-type carboxymethylcellulose which have been known to a person skilled in the art can be used. However, in order to obtain combined effects of the different disintegration mechanisms as shown above, it is preferable that a disintegrator having a superior effect to promote a mechanism other than "wicking" (e.g. "swelling") be used as the second disintegrator component. Suitable examples of such a disintegrator include crospovidone, sodium croscarmellose, sodium carboxymethyl starch, low substituted hydroxypropylcellulose, calcium carboxymethylcellulose, hydroxypropyl starch, and starch. Additionally, "crospovidone" is a common name for a cross-linked polymer of 1-vinyl-2-pyrrolidone, and "sodium croscarmellose" is a common name for a cross-linked product of sodium carboxymethylcellulose.

Among them, one, or any combination of two or more components selected from crospovidone, sodium croscarmellose, sodium carboxymethyl starch, low substituted hydroxypropylcellulose and calcium carboxymethylcellulose is preferable.

The disintegrative particulate composition comprises the excipient of sugars or sugar alcohols. Typical examples are mannitol, erythritol, xylitol, trehalose, lactose, maltose, maltitol, and sorbitol. Moreover, as preferable examples thereof, mannitol and lactose can be mentioned. As the excipient, two or more types of compounds properly selected from these compounds can also be used. Furthermore, one or more of the sugars or sugar alcohols optionally selected in the above group may be used.

The disintegrative particulate composition produced by the present invention further comprise crystalline cellulose known to a person skilled in the art. As typical examples of such a crystalline cellulose, commercially-available products such as "Avicel" (FMC Corporation), "CEOLUS" (Asahi Kasei Chemicals Corp.), and "VIVAPUR" (RETTENMAIER) can be mentioned.

Furthermore, various types of optional components known to a person skilled in the art may properly be added and mixed into the disintegrative particulate composition of the present invention, for the purpose of adjusting various characteristics such as the disintegrating force, binding force and ease in taking the tablet, without impairing the effects of the present invention according to the above-described four components. As examples of such components, fluidizing agents, inorganic excipients, sweetening agents, flavoring agents and coloring agents can be mentioned.

The amount of each component blended in the disintegrative particulate composition of the present invention can properly be determined by a person skilled in the art, depending on, for example, the type of the component, the type and purpose of the medicinal ingredient, which is a target to be used in the disintegrative particulate composition, or the purpose of the final product, i.e. the orally-disintegrating tablet. In general, relative to the total weight of the disintegrative particulate composition, the amount of the first disintegrator component is within a range of 10% to 50% by weight, the amount of the second disintegrator component is within a range of 1% to 20% by weight, the amount of the excipient of sugars or sugar alcohols is within a range of 30 to 88% by weight, and the amount of the crystalline cellulose is within a range of 1% to 40% by weight.

It is preferable that the disintegrative particulate composition of the present invention have the following physical properties:

(1) an average particle size of 50 to 160 microns; and
(2) a water content of 0.5% to 6% by weight.

In addition, these physical properties are measured by using the following methods and conditions.

The average particle size: 2 g of the disintegrative particulate composition is subjected to a measurement with a $\phi$75 mm automatic shaking sieve device (Type "M-2", Tsutsui Scientific Instruments Co., Ltd.).

The water content: 5 g of the disintegrative particulate composition is subjected to a measurement using a halogen water content measuring device (Type "HB43", METTLER TOLEDO K.K.).

The disintegrative particulate composition according to the present invention may be produced by any method known to a person skilled in the art. For example, it may be produced by a method comprising a first wet granulation step using any one or two of the three components other than the crystalline cellulose, a second wet granulation step using at least granules obtained in the first wet granulation step and the remaining one or two components not used in the first wet granulation step, and a third step of mixing the crystalline cellulose into granules obtained in the second wet granulation step.

Alternatively, it may be produced by a method comprising a first wet granulation step using any two or three of the four components, and a second wet granulation step using at least granules obtained in the first wet granulation step and the remaining one or two of the four components not used in the first wet granulation step. The crystalline cellulose may be used both in the first wet granulation and the second wet granulation step.

For example, the first wet granulation step may be carried out using one of the first and second disintegrator components, the excipient and the crystalline cellulose; and the other disintegrator component may be added in the second wet granulation step. Alternatively, the first wet granulation step may be carried out using one of the first and second disintegrator components, and the excipient; and the crystalline cellulose the other disintegrator component may be added in the second wet granulation step.

Furthermore, the disintegrative particulate composition according to the present invention may be produced by one wet granulation step using all of the four components together.

In each method of the above production method, each granulation step is carried out by a method in which each component is dispersed in the presence of water, and the dispersion is dried to form complexes, i.e. by a wet granulation process. As specific examples of a wet granulation process, spray methods such as spray drying, tumbling granulation, agitation granulation and fluidized-bed granulation; the freeze-drying method; kneading granulation, and the like can be mentioned. The composition can be produced by any of these methods known to a person skilled in the art.

Since disintegrators such as an acid-type carboxymethyl-cellulose are hydrophilic, by carrying out a manipulation of applying a physical force such as by agitation or the like in the presence of water according to wet granulation, the aggregated state in the dry powder converts into a state in which particles are more dispersed. Dispersion can most easily be carried out by the fluidized-bed granulation process in which dispersion by water spraying and drying are carried out, spray drying, tumbling granulation, agitation granulation, etc., and also, drying speeds in these methods are high. Therefore, these methods are preferable.

Among them, the fluidized-bed granulation process is a granulation method in which water, an aqueous solution including a binder, or the like is sprayed onto powder, while blowing the powder up by hot air, and, for example, adjustment of spraying conditions, etc. is easy in this method. Therefore, the fluidized-bed granulation process is the most preferable method.

A person skilled in the art can properly determine which two types of components among the three components other than the crystalline cellulose are used in the first wet granulation step in the method of the present invention, depending on their types, amounts, etc. For example, the first wet granulation step can be carried out by using either the first or second disintegrator component, and the excipient. Furthermore, the crystalline cellulose may be mixed with the other components at least one of the first or second wet granulation step.

Furthermore, a person skilled in the art can properly determine various conditions in each granulation step. such as the spraying speed, the supply air temperature, the exhaust temperature, and the air supply rate, depending on types or amounts of components, etc.

In each granulation step and the second wet granulation step, as a medium for the spray liquid, a solvent acceptable in pharmaceuticals or foods, such as water, ethanol, methanol or acetone, can be mentioned. Alternatively, as the spray liquid, for example, an aqueous solution in which less than 10% of the component(s) for the disintegrative particulate composition is dissolved can be mentioned, and, in particular, water or such an aqueous solution is preferable.

In the third step of the above method, the disintegrative particulate composition is finally obtained by mixing the crystalline cellulose with the granules obtained in the second wet granulation step. The crystalline cellulose may be added and mixed by any method or means known to a person skilled in the art, for example, mixing with air such as fluidized-bed and mechanical mixing such as V-type or double cone-type.

Various types of optional components, other than the above-described four components, which can be appropriately included in the disintegrative particulate composition of the present invention and which have been known to a person skilled in the art, may be properly added in each wet granulation step. Alternatively, these optional components may also be added and mixed in an appropriate additional granulation step.

Furthermore, the present invention also relates to an orally-disintegrating tablet including the disintegrative particulate composition obtained by the above-described production method and a medicinal ingredient. The orally-disintegrating tablet can include other pharmaceutically-acceptable optional components such as excipients, surfactants, lubricants, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia can be used. In addition, types of the medicinal ingredient and auxiliary agents included therein are not particularly limited. Also, the blending ratios of the disintegrative particulate composition, the medicinal ingredient and optional components are not particularly limited as long as the expected effects of the present invention are brought about, and the blending ratios can properly be determined by a person skilled in the art. The orally-disintegrating tablet can be formulated by any methods known to a person skilled in the art, for example, by tableting.

As already described above, the orally-disintegrating tablet of the present invention has superior tablet hardness and disintegrability. As preferable values, the orally-disintegrating tablet may be characterized by having a hardness of 50 to 150 N, more preferably 80 to 150 N, much more preferably 89 to 150 (N), and by having a disintegration time in water of 10 to 30 seconds, more preferably 10 to 21 seconds, much more preferably 10 to 18 seconds.

In addition, contents of all related art documents cited in the present specification are incorporated herein by reference.

Hereinafter, the present invention will more specifically be described with reference to Examples. However, the present invention is not considered to be limited to the Examples.

[Evaluation on Hardness and Disintegrability Tests]

With respect to each of tablets obtained in Examples and Comparative Examples, the hardness, the disintegration time in water and the disintegration time in the oral cavity were measured based on the methods described below. The results of measured hardnesses and disintegration times are shown in Table 1.

In addition, values of these physical properties were measured based on the following conditions/methods.

Hardness: a hardness (N) was measured with a Kiya hardness tester (Fujiwara Scientific Company Co., Ltd.).

Disintegration time in water: a disintegration time in water was measured with a disintegration tester (NT-4HF, TOYAMA SANGYO CO., LTD.) in accordance with the method described in the Japanese Pharmacopoeia (however, an auxiliary disk was not used).

The measurements for the hardness and disintegration time were each repeated six times, and average values thereof were regarded as measurement results.

Example 1

(Production of the Disintegrative Particulate Composition One Step)

280 g of mannitol (D-mannitol, Merck Ltd.), 75 g of carmellose (NS-300, GOTOKU CHEMICAL CO., LTD.), 100 g of a crystalline cellulose (CEOLUS PH-101, Asahi Kasei Chemicals Corp.) and 40 g of crospovidone (Polyplasdone INF-10, ISP Japan) were charged to a fluidized-bed granulator (LAB-1, Powrex Corporation), and 300 g of purified water was sprayed onto the resulting mixture at a rate of 12 g/minute to thereby obtain granules (a disintegrative particulate composition of the present invention). 0.5 parts by weight of magnesium stearate (Taihei Chemical Industrial Co. Ltd.) was added to 99.5 parts by weight of the obtained granules, and these were mixed. The mixture was then subjected to tableting at tablet compression forces of 6.0 kN and 10.0 kN with a simple tableting machine (HANDTAB-100, ICHIHASHI-SEIKI Co., Ltd.) to thereby obtain tablets having a diameter of 8.0 mm, R6.5, and a weight of 250 mg. In addition, the granules had the following values for physical properties: (1) an average particle size of 91 microns and (2) a water content of 2.9% by weight.

Example 2

(Production of the Disintegrative Particulate Composition Two Steps)

380 g of mannitol (D-mannitol, Merck Ltd.), 75 g of carmellose (NS-300, GOTOKU CHEMICAL CO., LTD.) and 40 g of crospovidone (Polyplasdone INF-10, ISP Japan) were charged to the fluidized-bed granulator (LAB-1, Powrex Corporation), and 300 g of purified water was sprayed onto the resulting mixture at a rate of 12 g/minute to thereby obtain granules. The granules had the following values for physical properties: (1) an average particle size of 65 microns and (2) a water content of 1.25% by weight. 80 parts by eight of the resulting granules and 20 parts by weight of the crystalline cellulose (CEOLUS PH-101, Asahi Kasei Chemicals Corp.) were mixed to thereby obtain granules (a disintegrative particulate composition of the present invention). The disintegrative particulate composition had the following values for physical properties: (1) an average particle size of 62 microns and (2) a water content of 1.8% by weight. 0.5 parts by weight of magnesium stearate (Taihei Chemical Industrial Co. Ltd.) was added to 99.5 parts by weight of the disintegrative particulate composition, and these were mixed. The mixture was then subjected to tableting at tablet compression forces of 6.0 kN and 10.0 kN with the simple tableting machine (HANDTAB-100, ICHI-HASHI-SEIKI Co., Ltd.) to thereby obtain tablets having a diameter of 8.0 mm, R6.5, and a weight of 250 mg.

Example 3

(Production of the Disintegrative Particulate Composition One Step)

280 g of lactose (lactose hydrate, Shizenkenko Co., Ltd.), 75 g of carmellose (NS-300, GOTOKU CHEMICAL CO., LTD.), 100 g of the crystalline cellulose (CEOLUS PH-101, Asahi Kasei Chemicals Corp.) and 40 g of crospovidone (Polyplasdone INF-10, ISP Japan) were charged to the fluidized-bed granulator (LAB-1, Powrex Corporation), and 300 g of purified water was sprayed onto the resulting mixture at a rate of 12 g/minute to thereby obtain granules (a disintegrative particulate composition of the present invention). The obtained disintegrative particulate composition was then subjected to tableting in the same way as in Example 1 to thereby obtain tablets having a diameter of 8.0 mm, R6.5, and a weight of 250 mg. In addition, the granules had the following values for physical properties: (1) an average particle size of 64 microns and (2) a water content of 3.0% by weight.

Example 4

(Production of the Disintegrative Particulate Composition One Step)

280 g of mannitol (D-mannitol, Merck Ltd.), 75 g of carmellose (NS-300, GOTOKU CHEMICAL CO., LTD.), 100 g of the crystalline cellulose (CEOLUS PH-101, Asahi Kasei Chemicals Corp.) and 40 g of sodium croscarmellose (ND-2HS, Asahi Kasei Chemicals Corp.) were charged to the fluidized-bed granulator (LAB-1, Powrex Corporation), and 300 g of purified water was sprayed onto the resulting mixture at a rate of 12 g/minute to thereby obtain granules (a disintegrative particulate composition of the present invention). The obtained disintegrative particulate composition was then subjected to tableting at tablet compression forces of 6.0 kN, 8.0 kN and 10.0 kN in the same way as in Example 1 to thereby obtain tablets having a diameter of 8.0 mm, R6.5, and a weight of 250 mg. In addition, the granules had the following values for physical properties: (1) an average particle size of 97 microns and (2) a water content of 3.2% by weight.

Example 5

(Production of the Disintegrative Particulate Composition One Step)

280 g of mannitol (D-mannitol, Merck Ltd.), 75 g of carmellose (NS-300, GOTOKU CHEMICAL CO., LTD.), 100 g of the crystalline cellulose (CEOLUS PH-101, Asahi Kasei Chemicals Corp.) and 40 g of sodium carboxymethyl starch (Primojel, DFE Pharma) were charged to the fluidized-bed granulator (LAB-1, Powrex Corporation), and 300 g of purified water was sprayed onto the resulting mixture at a rate of 12 g/minute to thereby obtain granules (a disintegrative particulate composition of the present invention). The obtained disintegrative particulate composition was then subjected to tableting at tablet compression forces of 6.0 kN and 8.0 kN in the same way as in Example 1 to thereby obtain tablets having a diameter of 8.0 mm, R6.5, and a weight of 250 mg. In addition, the granules had the following values for physical properties: (1) an average particle size of 90 microns and (2) a water content of 3.6% by weight.

Example 6

(Production of the Disintegrative Particulate Composition One Step)

280 g of mannitol (D-mannitol, Merck Ltd.), 75 g of carmellose (NS-300, GOTOKU CHEMICAL CO., LTD.), 70 g of the crystalline cellulose (CEOLUS PH-101, Asahi Kasei Chemicals Corp.) and 50 g of low substituted hydroxypropylcellulose (LH-20, Shin-Etsu Chemical Co., Ltd.) were charged to the fluidized-bed granulator (LAB-1, Powrex Corporation), and 300 g of purified water was sprayed onto the resulting mixture at a rate of 12 g/minute to thereby obtain granules (a disintegrative particulate composition of the present invention). The obtained disintegrative particulate composition was then subjected to tableting at tablet compression forces of 6.0 kN and 8.0 kN in the same way as in Example 1 to thereby obtain tablets having a diameter of 8.0 mm, R6.5, and a weight of 250 mg. In addition, the granules had the following values for physical properties: (1) an average particle size of 73 microns and (2) a water content of 3.6% by weight.

Example 7

(Production of the Disintegrative Particulate Composition One Step)

270 g of mannitol (D-mannitol, Merck Ltd.), 75 g of carmellose (NS-300, GOTOKU CHEMICAL CO., LTD.), 100 g of the crystalline cellulose (CEOLUS PH-101, Asahi Kasei Chemicals Corp.) and 50 g of hydroxypropyl starch (HPS-101W, Freund Corporation) were charged to the fluidized-bed granulator (LAB-1, Powrex Corporation), and 300 g of purified water was sprayed onto the resulting mixture at a rate of 15 g/minute to thereby obtain granules (a disintegrative particulate composition of the present invention). The obtained disintegrative particulate composition was then subjected to tableting at tablet compression forces of 6.0 kN and 8.0 kN in the same way as in Example 1 to thereby obtain tablets having a diameter of 8.0 mm, R6.5, and a weight of 250 mg. In addition, the granules had the following values for physical properties: (1) an average particle size of 75 microns and (2) a water content of 3.7% by weight.

Example 8

(Production of the Disintegrative Particulate Composition One Step)

300 g of mannitol (D-mannitol, Merck Ltd.), 75 g of carmellose (NS-300, GOTOKU CHEMICAL CO., LTD.), 70 g of the crystalline cellulose (CEOLUS PH-101, Asahi Kasei Chemicals Corp.) and 50 g of calcium carboxymethylcellulose (ECG-505, GOTOKU CHEMICAL CO., LTD.) were charged to the fluidized-bed granulator (LAB-1, Powrex Corporation), and 300 g of purified water was sprayed onto the resulting mixture at a rate of 12 g/minute to thereby obtain granules (a disintegrative particulate composition of the present invention). The obtained disintegrative particulate composition was then subjected to tableting at tablet compression forces of 6.0 kN in the same way as in Example 1 to thereby obtain tablets having a diameter of 8.0 mm, R6.5, and a weight of 250 mg. In addition, the granules had the following values for physical properties: (1) an average particle size of 154 microns and (2) a water content of 4.2% by weight.

Comparative Example 1 (without Carmellose)

355 g of mannitol (D-mannitol, Merck Ltd.), 100 g of the crystalline cellulose (CEOLUS PH-101, Asahi Kasei Chemicals Corp.) and 40 g of crospovidone (Polyplasdone INF-10, ISP Japan) were charged to the fluidized-bed granulator (LAB-1, Powrex Corporation), and 300 g of purified water was sprayed onto the resulting mixture at a rate of 12 g/minute to thereby obtain granules. The obtained disintegrative particulate composition was then subjected to tableting at tablet compression forces of 6.0 kN and 8.0 kN in the same way as in Example 1 to thereby obtain tablets having a diameter of 8.0 mm, R6.5, and a weight of 250 mg.

Comparative Example 2 (without Crystalline Cellulose)

380 g of mannitol (D-mannitol, Merck Ltd.), 75 g of carmellose (NS-300, GOTOKU CHEMICAL CO., LTD.) and 40 g of crospovidone (Polyplasdone INF-10, ISP Japan) were charged to the fluidized-bed granulator (LAB-1, Powrex Corporation), and 300 g of purified water was sprayed onto the resulting mixture at a rate of 12 g/minute to thereby obtain granules. The obtained disintegrative particulate composition was then subjected to tableting at tablet compression forces of 6.0 kN and 8.0 kN in the same way as in Example 1 to thereby obtain tablets having a diameter of 8.0 mm, R6.5, and a weight of 250 mg.

Comparative Example 3 (without Carmellose)

355 g of mannitol (D-mannitol, Merck Ltd.), 100 g of the crystalline cellulose (CEOLUS PH-101, Asahi Kasei Chemicals Corp.) and 40 g of sodium croscarmellose (ND-2HS, Asahi Kasei Chemicals Corp.) were charged to the fluidized-bed granulator (LAB-1, Powrex Corporation), and 300 g of purified water was sprayed onto the resulting mixture at a rate of 12 g/minute to thereby obtain granules. The obtained disintegrative particulate composition was then subjected to tableting at tablet compression forces of 6.0 kN, 8.0 kN and 10.0 kN in the same way as in Example 1 to thereby obtain tablets having a diameter of 8.0 mm, R6.5, and a weight of 250 mg.

Comparative Example 4 (without Crystalline Cellulose)

380 g of mannitol (D-mannitol, Merck Ltd.), 75 g of carmellose (NS-300, GOTOKU CHEMICAL CO., LTD.) and 40 g of sodium croscarmellose (ND-2HS, Asahi Kasei Chemicals Corp.) were charged to the fluidized-bed granulator (LAB-1, Powrex Corporation), and 300 g of purified water was sprayed onto the resulting mixture at a rate of 12 g/minute to thereby obtain granules. The obtained disintegrative particulate composition was then subjected to tableting at tablet compression forces of 6.0 kN, 8.0 kN and 10.0 kN in the same way as in Example 1 to thereby obtain tablets having a diameter of 8.0 mm, R6.5, and a weight of 250 mg.

Comparative Example 5 (without Carmellose)

355 g of mannitol (D-mannitol, Merck Ltd.), 100 g of the crystalline cellulose (CEOLUS PH-101, Asahi Kasei Chemicals Corp.) and 40 g of sodium carboxymethyl starch (Primojel, DFE Pharma) were charged to the fluidized-bed granulator (LAB-1, Powrex Corporation), and 300 g of purified water was sprayed onto the resulting mixture at a rate of 12 g/minute to thereby obtain granules. The obtained disintegrative particulate composition was then subjected to tableting at tablet compression forces of 6.0 kN and 8.0 kN in the same way as in Example 1 to thereby obtain tablets having a diameter of 8.0 mm, R6.5, and a weight of 250 mg.

Comparative Example 6 (without Crystalline Cellulose)

380 g of mannitol (D-mannitol, Merck Ltd.), 75 g of carmellose (NS-300, GOTOKU CHEMICAL CO., LTD.) and 40 g of sodium carboxymethyl starch (Primojel, DFE Pharma) were charged to the fluidized-bed granulator (LAB-1, Powrex Corporation), and 300 g of purified water was sprayed onto the resulting mixture at a rate of 12 g/minute to thereby obtain granules. The obtained disintegrative particulate composition was then subjected to tableting at tablet compression forces of 6.0 kN and 8.0 kN in the same way as in Example 1 to thereby obtain tablets having a diameter of 8.0 mm, R6.5, and a weight of 250 mg.

TABLE 1

| Tablet | Example 1 | | Example 2 | | Example 3 | |
|---|---|---|---|---|---|---|
| Tablet compression force (kN) | 6.0 | 10.0 | 6.0 | 10.0 | 6.0 | 10.0 |
| Hardness (N) | 59 | 98 | 53 | 89 | 60 | 100 |
| Disintegration time in water (seconds) | 12 | 15 | 13 | 18 | 18 | 21 |

| Tablet | Comparative Example 1 | | Comparative Example 2 | |
|---|---|---|---|---|
| Tablet compression force (kN) | 6.0 | 8.0 | 6.0 | 8.0 |
| Hardness (N) | 69 | 100 | 34 | 53 |
| Disintegration time in water (seconds) | 24 | 26 | 21 | 20 |

TABLE 2

| Tablet | Example 4 | | |
|---|---|---|---|
| Tablet compression force (kN) | 6.0 | 8.0 | 10.0 |
| Hardness (N) | 60 | 83 | 99 |
| Disintegration time in water (seconds) | 14 | 18 | 24 |

| Tablet | Comparative Example 3 | | | Comparative Example 4 | | |
|---|---|---|---|---|---|---|
| Tablet compression force (kN) | 6.0 | 8.0 | 10.0 | 6.0 | 8.0 | 10.0 |
| Hardness (N) | 69 | 86 | 97 | 25 | 32 | 36 |
| Disintegration time in water (seconds) | 19 | 21 | 28 | 15 | 16 | 19 |

TABLE 2-continued

| Tablet | Example 5 | |
|---|---|---|
| Tablet compression force (kN) | 6.0 | 8.0 |
| Hardness (N) | 50 | 69 |
| Disintegration time in water (seconds) | 16 | 21 |

| Tablet | Comparative Example 5 | | Comparative Example 6 | |
|---|---|---|---|---|
| Tablet compression force (kN) | 6.0 | 8.0 | 6.0 | 8.0 |
| Hardness (N) | 66 | 84 | 18 | 26 |
| Disintegration time in water (seconds) | 26 | 34 | 15 | 17 |

TABLE 3

| Tablet | Example 6 | | Example 7 | | Example 8 |
|---|---|---|---|---|---|
| Tablet compression force (kN) | 6.0 | 8.0 | 6.0 | 8.0 | 6.0 |
| Hardness (N) | 58 | 79 | 65 | 85 | 55 |
| Disintegration time in water (seconds) | 14 | 18 | 15 | 19 | 17 |

When comparing Examples 1 to 3 with Comparative Example 1 (without carmellose) in Table 1, it was proven that the orally-disintegrating tablet including the disintegrative particulate composition comprising the four components consisting of the first disintegrator component of the acid-type carboxymethylcellulose, the second disintegrator component other than the acid-type carboxymethylcellulose, the excipient of a sugar or sugar alcohol, and crystalline cellulose has a rapid disintegrability in spite of a high tablet hardness. It was also proven that the orally-disintegrating tablets of Examples 1 to 3 have such an excellent moldability that the high tablet hardness can be obtained by a smaller tablet compression force. Similar results were obtained as shown in Table 2 by the comparison between Example 4 and Comparative Example 3 (without carmellose); and between Example 5 and Comparative Example 5 (without carmellose). Also, similar results were shown by the comparison between Example 4 and Comparative Example 4 (without crystalline cellulose); and between Example 5 and Comparative Example 6 (without crystalline cellulose).

Furthermore, Examples 6, 7 and 8 in Table 3 have also proven that the orally-disintegrating tablet including the disintegrative particulate composition according to the present invention has the rapid disintegrability in spite of high tablet hardness.

INDUSTRIAL APPLICABILITY

The present invention significantly contributes to research and development of orally-disintegrating tablets having the excellent tablet hardness and disintegrability.

The invention claimed is:

1. A disintegrative particulate composition comprising:
   a first disintegrator component of an acid-type carboxymethylcellulose,
   a second disintegrator component other than the acid-type carboxymethylcellulose,
   an excipient of a sugar or sugar alcohol, and
   crystalline cellulose having a bulk density of 0.26-0.31 g/cm$^3$,
   wherein the second disintegrator component comprises one or more components selected from the group consisting of crospovidone, sodium croscarmellose, sodium carboxymethyl starch, calcium carboxymethylcellulose, and hydroxypropyl starch.

2. An orally-disintegrating tablet, including the disintegrative particulate composition according to claim 1 and a medicinal ingredient.

3. The orally-disintegrating tablet according to claim 2, having a hardness of 50 to 150 N and a disintegration time in water of 10 to 30 seconds.

* * * * *